United States Patent
Breznock et al.

(10) Patent No.: US 7,326,197 B2
(45) Date of Patent: Feb. 5, 2008

(54) METHOD AND APPARATUS FOR CHEST DRAINAGE

(76) Inventors: Eugene M. Breznock, 27956 State Highway 128, Winters, CA (US) 95694; Jay A. Lenker, 408 Panorama Dr., Laguna Beach, CA (US) 92651

( * ) Notice: Subject to any disclaimer, the term of this patent is extended or adjusted under 35 U.S.C. 154(b) by 308 days.

(21) Appl. No.: 10/694,510

(22) Filed: Oct. 27, 2003

(65) Prior Publication Data

US 2004/0087905 A1   May 6, 2004

Related U.S. Application Data

(63) Continuation of application No. 09/908,316, filed on Jul. 17, 2001, now Pat. No. 6,638,253.

(51) Int. Cl.
 *A61M 1/00* (2006.01)
 *A61M 27/00* (2006.01)
 *A61M 37/00* (2006.01)
(52) U.S. Cl. ............... 604/541; 604/131; 604/164.04; 604/247
(58) Field of Classification Search ............................... 604/164.01–167.05, 500, 508, 509, 523, 604/528, 540, 541, 543, 915, 244–249
See application file for complete search history.

(56) References Cited

U.S. PATENT DOCUMENTS

| | | | | |
|---|---|---|---|---|
| 4,036,231 A * | 7/1977 | Dodge et al. | ............... | 604/321 |
| 5,370,899 A * | 12/1994 | Conway et al. | ............... | 427/2.3 |
| 5,419,776 A * | 5/1995 | Baer | .......................... | 604/246 |
| 5,509,909 A * | 4/1996 | Moy | .......................... | 604/540 |
| 5,800,409 A * | 9/1998 | Bruce | ...................... | 604/523 |
| 5,897,531 A * | 4/1999 | Amirana | .................... | 604/180 |
| 5,957,913 A * | 9/1999 | de la Torre et al. | ............ | 606/1 |
| 5,997,526 A * | 12/1999 | Giba et al. | .................. | 604/531 |
| 6,669,708 B1 * | 12/2003 | Nissenbaum et al. | ........ | 606/153 |
| 6,770,070 B1 * | 8/2004 | Balbierz | ...................... | 606/41 |
| 2002/0161353 A1* | 10/2002 | Kortelling | .................. | 604/528 |

* cited by examiner

*Primary Examiner*—Tatyana Zalukaeva
*Assistant Examiner*—Melanie J Hand

(57) ABSTRACT

The present invention describes a device for placement in the thoracic cavity of a patient. The device is a cannula, tube or catheter for chest drainage. The device serves as a conduit for drainage of excessive fluid or air buildup in the chest to a receptacle outside the body. The device also serves to prevent influx of fluid or air into the chest cavity, thus preventing pneumothorax or infection. The device incorporates systems for anchoring the chest drainage cannula to the chest and for steering the chest drainage cannula into the thoracic cavity.

20 Claims, 5 Drawing Sheets

METHOD AND APPARATUS FOR CHEST DRAINAGE

PRIORITY CLAIM

This application is a continuation of U.S. application Ser. No. 09/908,316, filed on Jul. 17, 2001, now U.S. Pat. No. 6,638,253.

FIELD OF THE INVENTION

The field of this invention is general surgery, thoracic surgery, trauma and critical care.

BACKGROUND OF THE INVENTION

Chest drainage tubes are used following thoracic surgery, chest trauma or to treat certain medical conditions. The purpose of a chest tube is to remove buildup of excessive body fluids, contaminants or air from the thoracic cavity. The presence of an opening into the chest or thorax, created with or without a cannula will cause pneumothorax (collapsed lung). Negative pressure in the chest cavity is created by the chest muscles and diaphragm in order to cause lung expansion and resulting inspiration of a breath. Therefore, a hole in the chest will equalize pressure and prevent critical lung function, i.e. lung insufflation. Any cannula placed into a patient's chest cavity for drainage must be sealed to prevent pneumothorax from occurring.

Current chest drainage cannulae, also called chest tubes, drainage catheters or drainage cannulae, are flexible polymer tubes, placed into the chest cavity and extending outside the patient.

Chest drainage tubes are placed using a surgically invasive procedure. Generally, if a surgical incision into the chest has not been made, the chest tube is usually placed with the aid of an internal trocar that stiffens the chest tube and allows for easier chest wall penetration during placement. The procedure begins with a skin incision large enough to accommodate the diameter of the selected chest tube. Chest tubes are typically 8 mm to 10 mm diameter. The internal trocar, having a sharp point, is placed inside the chest tube. The pointed end of the trocar chest tube combination is pressed through the skin incision and plunged into the thoracic cavity through the muscle, fascia and fat layers of the patient, through the rib space and into the pleural cavity. The trocar is removed and the chest tube is clamped to prevent pneumothorax.

When drainage is required, the clamp is opened and fluid, air and contaminants are removed from the thoracic cavity. The fluid, air and contaminants typically are removed, forcefully, by use of external vacuum or pumping systems. The clamp is closed once drainage is completed to avoid reflux of fluid and air back into the chest cavity and possible generation of pneumothorax or influx of contaminants (i.e. infectious agents).

Placement of current chest drainage tubes is an invasive surgical procedure. With any invasive surgical procedure, there exists a risk of iatrogenic trauma to the patient. Significant training is required to safely perform these procedures and this training may not have been completed by emergency personnel who are the first line of treatment for many patients experiencing trauma.

Improved valving mechanisms would increase functionality of chest drainage tubes and overcome issues that occur with clamp application and removal. There are also fewer steps required of the medical practitioner in chest drainage when a tube with an internal valving mechanism is employed. There may also be a problem with a chest tube being pushed too far into the patient, resulting in kinking, compromised drainage and potential iatrogenic damage to internal organs.

SUMMARY OF THE INVENTION

This invention relates to a catheter, tube or cannula for draining fluid, air and contaminants from the chest and a method of placement.

The cannula of the present invention includes an internal, semi-automatic valving mechanism, which allows for fewer steps and minimizes the chance of leaving the chest tube open to atmosphere when drainage is completed. The cannula of the present invention also comprises an external movable fixation device to prevent inadvertently pushing the cannula too far into the patient. The minimally invasive placement method of the present invention is beneficial in not only the emergency setting but also in the hospital setting by reducing the chance of iatrogenic injury to the patient.

The cannula is a polymeric tube, preferably with a metal spiral winding to prevent kinking or collapse, which is fenestrated at or near the distal tip at a plurality of sites. The cannula includes an interior valve or seal, located inside the drainage lumen of the cannula, operably able to prevent reflux or efflux of fluid, air and contaminants to or from the chest. The cannula includes an intracorporeal fixation device, located internal to the patient, to prevent outward dislodgement of the chest tube from the chest. The cannula also includes an extracorporeal fixation device, located external to the patient to prevent inward movement of the chest tube.

In one embodiment, application of a vacuum at the proximal end of the cannula causes the internal valve to open thus allowing free flow of fluid, air and contaminants from the chest through the cannula and into the drainage system. The drainage system is typically a vacuum powered, water sealed suction device and collection reservoir. Removal of the vacuum causes exposure of the valve to atmospheric pressure and subsequent closure of the valve, thus reflux of fluid, air and contaminants into the chest is prevented.

Alternatively, the valve could be operated by application of positive pressure (above atmospheric) for closure of the valve and application of negative or zero pressure to open the valve. External feedback systems utilizing pressure sensors or other devices are used to ensure patient safety with the positive pressure valve closure embodiment.

In another embodiment, the internal valve is placed at the proximal end of the cannula. This valve is fabricated from a soft polymeric compound or foam with a central hole that is normally closed. Application of a mechanical force through the center of the valve, with a hollow obturator, for example, opens the valve and allows flow through the hollow obturator. Removal of the hollow obturator causes closure of the valve and prevention of reflux back into the thoracic cavity.

In yet another embodiment, the valve is a duckbill valve that passively prevents reflux back into the thoracic cavity while allowing drainage from the chest cavity under application of appropriate pressure drop across the valve. Such pressure drop can occur from an increase of intrapleural pressure caused by buildup of fluids or by application of a vacuum to the outlet side of the valve.

In all embodiments, the valve systems are, preferably, integral to the cannula and unable to be separated from the cannula when, for example, the patient rolls over and stresses the connection.

The drainage cannula of the present invention includes an intracorporeal fixation or retaining device that prevents the cannula from being removed inadvertently from the patient. This intracorporeal device is, for example, an elastomeric or inelastic (i.e. angioplasty-type) balloon affixed to the exterior surface of the cannula. The balloon is passed inside the chest cavity and is inflated with sterile liquids or air to prevent withdrawal through the hole or wound in the chest wall. Inflation typically occurs using a balloon inflation lumen in the cannula, inflation ports between the lumen and the balloon, and an inflation device external to the cannula.

Additionally, the drainage cannula of the present invention includes an extracorporeal fixation device that may comprise one or more clips that are affixed to the exterior of the cannula in a movable fashion. These clips are, preferably, located proximally to the internal fixation device or balloon. They may be moved against the chest wall and frictionally engaged to the cannula shaft to prevent the cannula from being forced too far into the patient. Such extracorporeal fixation devices could be retrofitted to existing chest tubes to improve the functionality of existing chest tubes.

The chest drainage tube of the current invention is placed in a minimally invasive procedure. Placement is accomplished by first performing a surgical skin nick and then placing a hypodermic needle into the pleural space of the patient at the site of the skin nick. A J-tip guidewire is placed through the hypodermic needle and the hypodermic needle is removed. A percutaneous access device or trocar is placed into the central lumen of the chest tube and over the guidewire and routed into the pleural space.

In a further embodiment, the cannula is steerable. This is accomplished by use of a malleable, bendable trocar that can be shaped prior to insertion into the patient. In another embodiment, steerability is obtainable by heat setting the cannula with a curved shape. Axially moving a rigid straight trocar into the bent portion of the cannula from the proximal end causes the curved shape to straighten out. This controllable bending is useful for negotiating tight turns in the patient. In another embodiment, steerability may be obtained using actuators on the surface or within the interior of the cannula to force bending of the cannula. These actuators are typically electrically powered. An actuator comprises electrical leads, a power source, a compressible substrate, and shape memory materials such as nitinol. Such actuators may be distributed along the length of the cannula. The actuators may be placed so as to oppose each other. Opposing actuators are activated one at a time and not simultaneously.

The combination of minimally invasive placement and reduced steps to operate the chest drainage tube will benefit patients and medical practitioners by reducing errors, minimizing trauma, increasing ease of use, and improving patient outcomes.

DETAILED DESCRIPTION OF THE INVENTION

Figure 1:
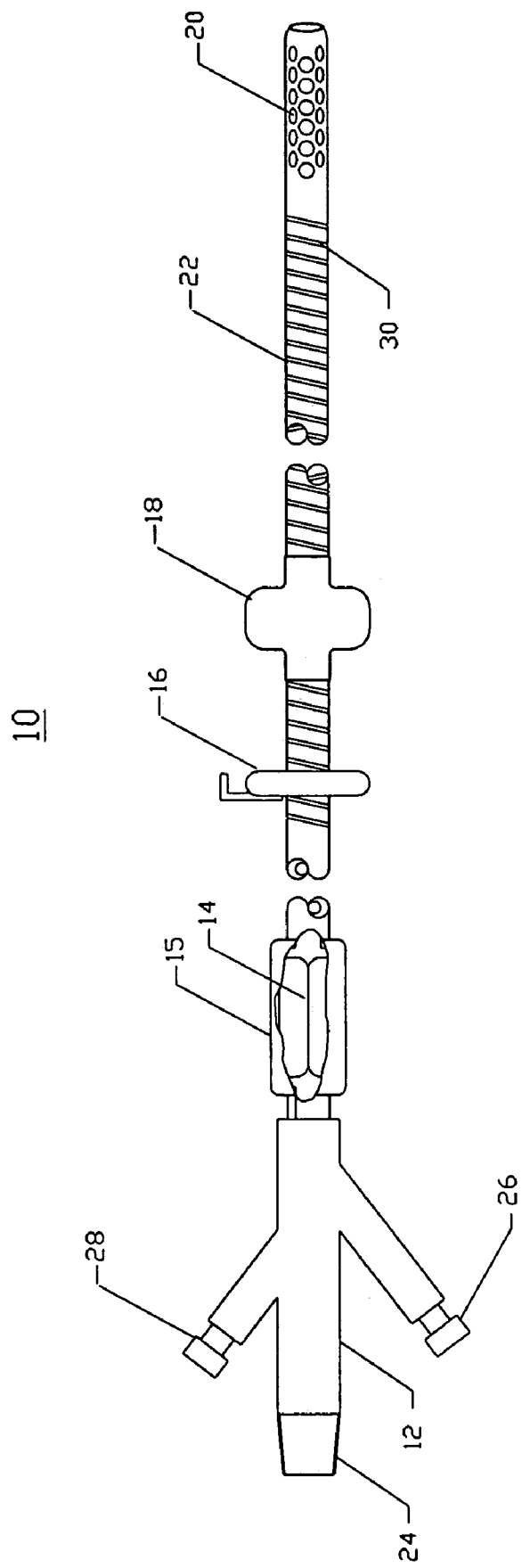
FIG. 1 illustrates the cannula, according to aspects of an embodiment of the invention.

FIG. 1 illustrates a cannula, tube or catheter 10 of the present invention. The catheter 10 comprises a manifold or hub 12, a bidirectional or two-way valve or seal 14, an extracorporeal fixation device 16, an intracorporeal fixation device 18, a plurality of drainage holes 20, and a length of multi-lumen tubing 22. In addition, the catheter 10 optionally comprises a valve housing 15. The manifold 12 comprises a drainage adapter or fitting 24, a valve-enabling adapter or fitting 26, and an intracorporeal fixation-enabling adapter or fitting 28. In this preferred embodiment, the intracorporeal fixation device 18 is a balloon, and the intracorporeal fixation-enabling adapter 28 is a balloon inflation adapter or fitting. The multi-lumen tubing preferably comprises a stiffening wire 30.

Figure 2:
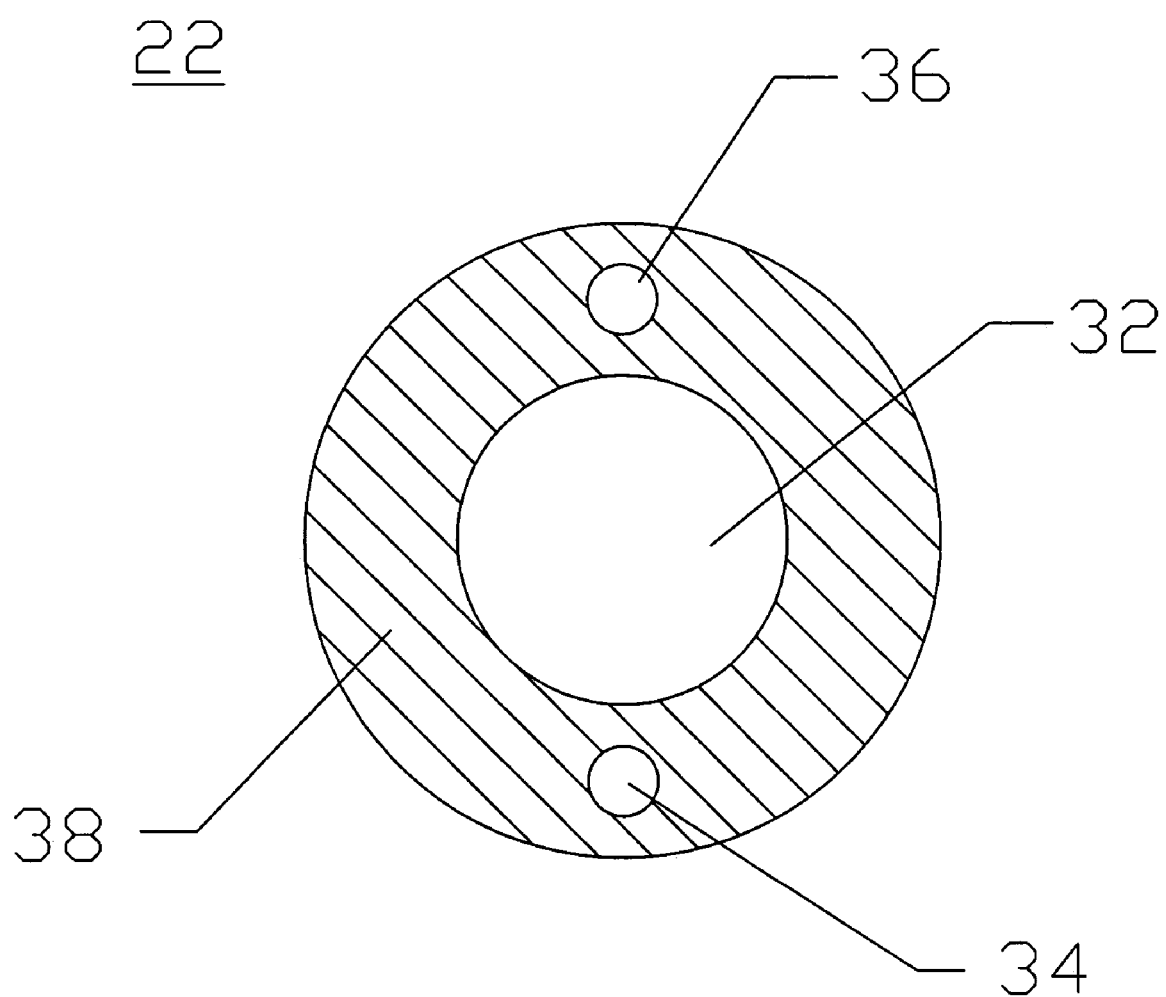
FIG. 2 illustrates a cross-section of multi-lumen tubing used in fabrication of the cannula, according to aspects of an embodiment of the invention.

FIG. 2 illustrates a cross-section of the multi-lumen tubing 22. The multi-lumen tubing 22 comprises a drainage lumen 32, a valve enabling lumen 34, an intracorporeal fixation-enabling lumen 36, and a wall 38. In this preferred embodiment, the intracorporeal fixation-enabling lumen 36 is an inflation lumen. There is no communication between the drainage lumen 32, the inflation lumen 36 and the valve enabling lumen 34. The tubing material may be selected from any polymer such as, but not limited to, polyvinyl chloride, polyurethane, polyethylene and the like. The tubing 22 is, preferably, transparent or semi-transparent. At least a portion of the tubing 22 is preferably stiffened with a helical winding of material such as stainless steel, nitinol and the like. The stiffening 30 could also be created using corrugations in the tubing 22 or by addition of a strong polymer such as glass-filled polycarbonate instead of the metal helical winding. The stiffening member 30 serves the purpose of preventing collapse of the cannula 10 when vacuum is applied to the drainage lumen 32. The stiffening member 30 also serves to prevent kinking when the cannula 10 is bent around a tight radius.

Referring to FIGS. 1 and 2, the manifold 12 connects to the proximal end of the length of multi-lumen tubing 22 such that the drainage adapter 24 connects to the drainage lumen 32, the balloon inflation adapter 28 connects to the inflation lumen 36, and the valve-enabling adapter 26 connects to the valve-enabling lumen 34. There is no communication between the drainage adapter 24, the balloon inflation adapter 28, and the valve-enabling adapter 26. The manifold 12 is typically molded from polymer, such as polyvinyl chloride, polycarbonate, acrilonitrile butadiene styrene (ABS), or the like.

The distal end of the multi-lumen tubing 22 comprises the plurality of drainage holes 20. The drainage holes 20 connect the exterior of the catheter 10 with the drainage lumen 32. The holes 20 are of sufficient size and quantity to allow for passage of fluid, thrombus and debris that might need to be removed from the chest cavity. The plurality of drainage holes 20 and the drainage lumen 32 may further be coated with an anti-thrombogenic coating of material such as, but not limited to, heparin.

The bidirectional valve or seal 14 is preferably located in the drainage lumen 32 of the catheter 10, between the manifold 12 and the drainage holes 20. Alternatively, the bidirectional valve or seal 14 may be mounted proximal to the manifold 12 or inside the manifold 12. If the optional valve housing 15 is used, the housing 15 encircles the catheter 10 and is open to the drainage lumen 32. The bidirectional valve 14 sets inside the housing 15 The intracorporeal fixation balloon 18 is located on the outside surface of the multi-lumen tubing 22, between the manifold 12 and the drainage holes 20, approximately 2 cm to 40 cm from the most proximal drainage hole. More preferably, the intracorporeal fixation device or balloon 18 is located between 5 cm and 20 cm from the most distal drainage hole. The balloon 18 is located over a balloon inflation port that allows communication between the balloon 18 and the inflation lumen 36. The extracorporeal fixation device 16 is slidably located on the outside of the multi-lumen tubing 22, between the manifold 12 and the intracorporeal fixation balloon 18.

When the catheter 10 is in use, the manifold 12 connects to a drainage system through the drainage adapter 24. The drainage adapter 24 is typically larger in diameter than the balloon inflation fitting 28 or valve-enabling fitting 26. The drainage adapter 24 is capable of being connected to the gravity-fed, pump-driven or vacuum-fed drainage system and is most typically a ⅜ inch to ½ inch diameter hose barb. Standard drainage systems generally comprise a connector, a length of tubing and a reservoir. Optionally, a vacuum pump may be connected to the reservoir.

The manifold 12 also connects to an inflation system through the balloon inflation adapter 28. The balloon inflation adapter 28 is typically a female luer fitting but may be any fluid-tight fitting suitable for use with an inflation syringe or the like. The standard balloon inflation system comprises a syringe, a volume of balloon inflation fluid such as sterile saline, air or radiopaque media, and a valve or stopcock. Additionally, the balloon inflation system could comprise a device, such as a jackscrew, to advance or withdraw a plunger on the syringe using mechanical advantage.

Additionally, the manifold 12 connects to a valve enabling system through the valve-enabling adapter 26. The valve-enabling adapter 26 is, preferably, a female luer lock adapter, but could be another type of fluid-tight connection such as a threaded swage-lock, or the like.

Figure 3A:
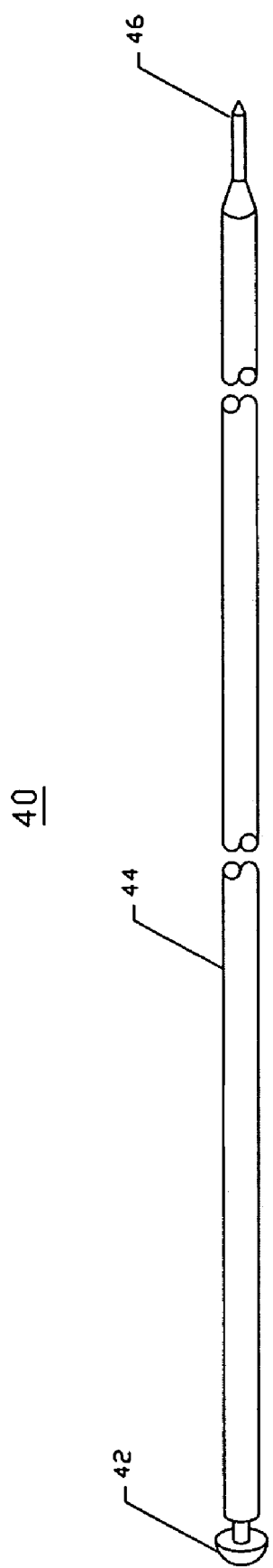
FIG. 3A illustrates a trocar useful for surgical placement of the cannula, according to aspects of an embodiment of the invention.
Figure 3B:
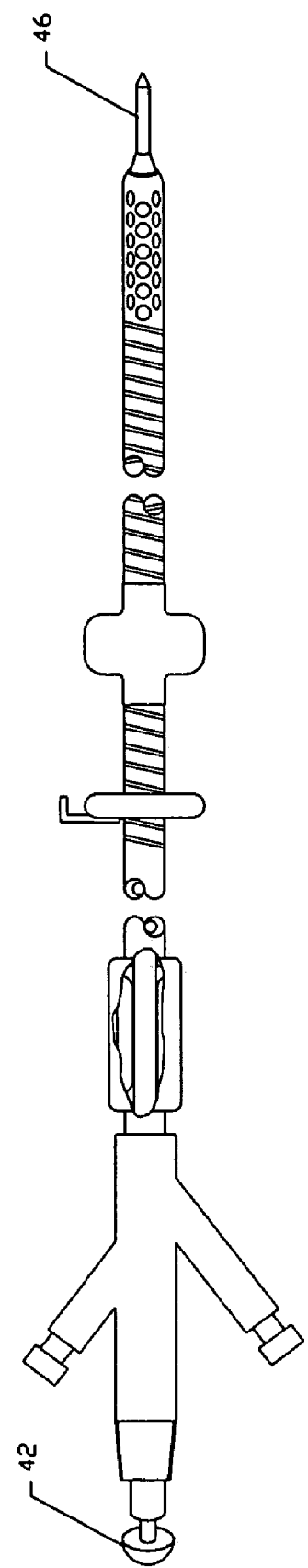
FIG. 3B illustrates the cannula with the trocar of FIG. 3A inserted therein, according to aspects of an embodiment of the invention.

FIG. 3A illustrates a trocar 40 useful for surgical placement of the cannula 10 of the present invention. The trocar 40 comprises a plunger 42, a body 44 and a pointed tip or needle 46. FIG. 3B shows the trocar 40 inserted into the drainage lumen 32 of the catheter 10. The needle 46 extends out from the distal tip of the catheter 10 and the plunger 42 extends out from the proximal end of the catheter 10. The internal trocar 40 stiffens the chest tube 10 and allows for easier thoracic penetration during placement. The internal trocar 40 is typically made from metal or polymer. The internal trocar 40 is, optionally, fabricated to be malleable. Medical personnel make a skin incision large enough to accommodate the diameter of the chest tube 10. Chest tubes 10 are typically 8 mm to 10 mm diameter. The pointed needle 46 of the trocar chest tube combination 40, 10 is pressed against the skin incision. Medical personnel push the plunger 42 to force the needle 46 into the thoracic cavity through the muscle, fascia and fat layers of the patient, through the rib space and into the pleural cavity. The trocar 40 is removed and the chest drainage tube 10 is in place. Fixation devices are enabled at this point.

Figure 4A:
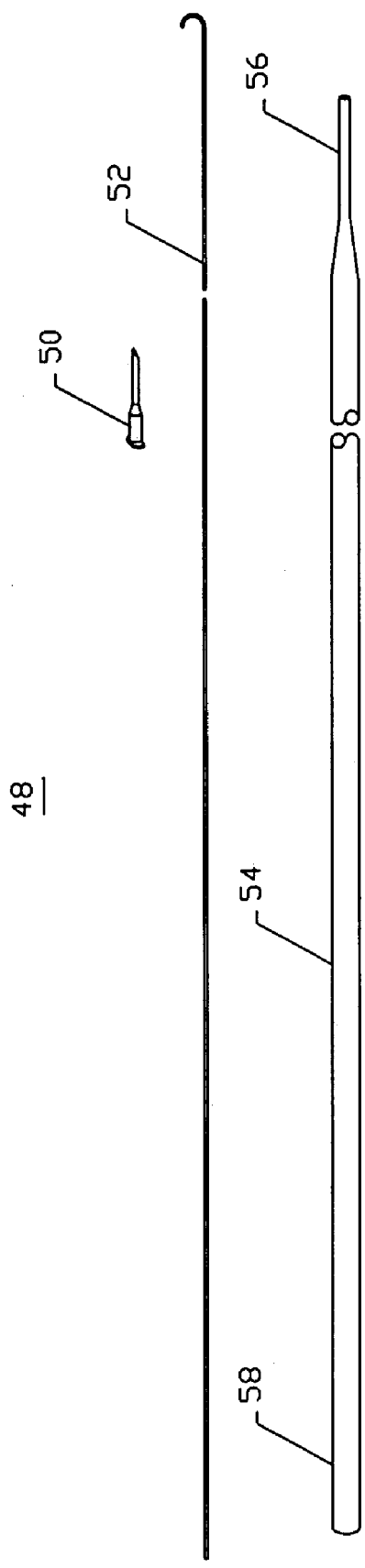
FIG. 4A illustrates the percutaneous access trocar, guidewire and hollow needle for the method, according to aspects of an embodiment of the invention.
Figure 4B:
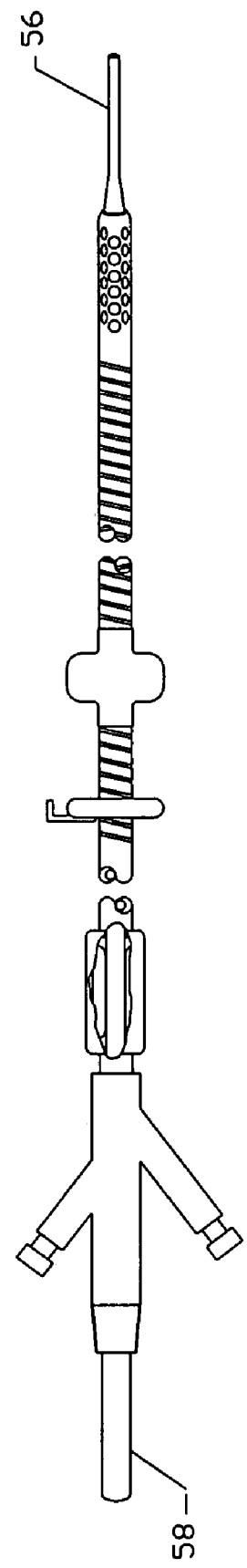
FIG. 4B illustrates the cannula with the percutaneous access trocar of FIG. 4A inserted therein, according to aspects of an embodiment of the invention.

FIGS. 4A and 4B illustrate a more preferred method of chest drainage tube placement. FIG. 4A illustrates a kit 48 comprising a hollow needle 50, a guidewire 52, and a tapered, flexible trocar 54. The trocar 54 comprises a tip 56 and a handle 58. First, the hollow needle 50 is inserted into the chest between the ribs, through the skin, fat, intercostal muscle, fascia and pleura. Next, the guidewire 52 is inserted through the needle 50 into the chest cavity to the desired location of the distal tip of the cannula 10 or beyond. Preferably, the guidewire 52 has a J-tip configuration at its distal end.

As shown in FIG. 4B, the tapered, flexible trocar 54 is inserted into the cannula 10 such that the tip 56 of the trocar 54 extends through the distal tip of the cannula 10 and the handle 58 of the trocar 54 extends through the proximal end of the cannula 10. The needle 50 is removed and the flexible trocar-cannula combination 54, 10 is threaded over the proximal end of the guidewire 52. The flexible trocar-cannula combination 54, 10 is moved over the guidewire 52 and inserted through the hole in the chest formed by the needle 50. The tapered trocar 54 expands the chest hole and allows passage of the larger diameter back section of trocar 54 and cannula 10 into the patient. The trocar 54 and cannula 10 are advanced to the desired intrathoracic site along the route described by the guidewire. Once the tip 56 of the trocar 54 is in the desired location, the trocar 54 is removed from the proximal end of the cannula 10. This method of cannula placement using the flexible, tapered trocar 54 requires a smaller incision than a standard trocar 40. The incision may even be a percutaneous stick. The additional benefit is that the flexible trocar 54 and cannula 10 follow the path created by the guidewire 52 and route to the desired location without damaging tissue inadvertently. The tapered, flexible trocar 54 is typically fabricated from polymers such as PVC or polyethylene. The tapered, flexible trocar 54 exhibits column strength but is bendable. The tapered, flexible trocar 54 is able to flex easily along the path described by the guidewire 52.

Referring to FIGS. 1 and 2, once the chest drainage tube 10 is placed in the patient's chest, the intracorporeal fixation balloon 18 is inflated. Balloon inflation fluid from the balloon inflation system is injected into the balloon inflation lumen 36 through the balloon inflation fitting 28. The balloon inflation fluid travels through the balloon inflation lumen 36 to the balloon inflation port. The balloon inflation fluid travels through the balloon inflation port into the balloon 18, inflating the intracorporeal fixation balloon 18. The valve or stopcock on the balloon inflation system is closed to maintain the balloon 18 in the inflated configuration. The stopcock remains attached to the balloon inflation adapter to prevent unwanted balloon deflation. The balloon 18 is inside the patient's chest and is larger than the chest incision. The balloon 18 prevents the chest drainage tube 10 from inadvertently being pulled out of the patient. The balloon inflation fluid is selectively drained from the intracorporeal fixation balloon 18 by opening the stopcock to deflate the balloon 18 and allow the cannula 10 to be removed from the patient's chest.

In another embodiment, the intracorporeal fixation device 18 is an expandable region of cylindrical material With longitudinal slits or slots, a distal ring and a proximal ring. The rings and interconnecting slotted cylinder are disposed coaxially and concentrically around the cannula 10 shaft. The distal ring is connected to a control rod routed through the intracorporeal fixation lumen 36 to a control handle on the proximal end of the cannula 10. When the cannula 10 is in place, the control rod is pulled, causing the distal ring of the intracorporeal fixation device 18 to pull along the cannula 10 shaft, toward the proximal ring. This causes the slit cylinder to collapse in length and the cylinder material between slits expands in diameter, forming a starburst pattern. A locking mechanism at the proximal end of the cannula 10 keeps the control rod from moving once the intracorporeal fixation device 18 is opened in the desired position. This system functions like a moly-bolt or drywall anchor to keep the cannula 10 from being removed from the chest inadvertently. The control rod may be unlocked and the distal ring advanced distally to contract the anchor around the cannula 10 so the cannula 10 may be removed from the patient. Optionally, holes or openings in the cannula 10 that connect with the drainage lumen 32 may be disposed underneath the slots or slits of the intracorporeal fixation device 18 thus providing additional chest drainage ports when the intracorporeal fixation device 18 is in the open position.

In addition to enabling the intracorporeal fixation device 18, the extracorporeal fixation device 16 is also enabled once the catheter 10 is in place in the patient's chest. The extracorporeal fixation device 16 is located outside the chest and is disabled to allow the fixation device 16 to slide over the exterior of the catheter 10, into place, against or close to the patient's skin. The extracorporeal fixation device 16 is enabled and forcibly stops sliding, preventing the chest drainage tube 10 from inadvertently being pushed farther into the patient's chest.

In a preferred embodiment, the extracorporeal fixation device 16 is a lockable clip device. When the lock is open, the extracorporeal fixation device 16 slides over the catheter 10. When the desired location on the catheter 10 is reached, the lock is closed and the extracorporeal fixation device 16 engages the catheter 10 with enough force to make dislodgement of the fixation device 16 relative to the cannula or catheter 10 difficult, but with insufficient force to crimp or restrict the catheter 10 or the lumens 32,34,36. The clip 16 is considerably larger than the diameter of the catheter 10 and the incision in the chest and, preferably has atraumatic rounded edges where it contacts the patient. At least one lateral dimension of the external fixation device or clip 16 is generally between 0.25 and 2 inches. More preferably, the external fixation device or clip 16 is between 0.5 and 1.0 inches in lateral dimension.

In another embodiment, the extracorporeal fixation device 16 is an inflatable balloon. The extracorporeal fixation balloon 16 may be inflated from the balloon inflation lumen 36 used to inflate the intracorporeal inflation balloon 18. Alternatively, the extracorporeal inflation balloon 16 may be inflated from an additional balloon inflation lumen.

In yet another embodiment, the extracorporeal fixation device 16 is an opposably engaged spring clip, which encircles the catheter 10. When the spring is compressed, the clip 16 is slid to the desired location on the catheter 10. When the pressure on the spring is released, the clip 16 is locked into place on the catheter 10. A similar type of spring clip is used to secure a drawstring on a sleeping bag. A further embodiment of the extracorporeal fixation device 16 is a rocking clip that slides when it is tilted relative to the lateral axis of the cannula 10 and locks when it is in the plane perpendicular to the axis of the cannula 10.

In another embodiment, the extracorporeal fixation device 16 comprises a penetrable polymeric tab to allow suture passage and attachment of the extracorporeal fixation device 16 to the patient's skin with suture. The distal side of the extracorporeal fixation device 16 may comprise an adhesive layer to facilitate not only fixation but provide a contamination barrier at the entry site. The extracorporeal fixation device 16 optionally comprises a hole located somewhere on its structure, through which suture may be passed to facilitate attachment to the patient's skin.

In yet another embodiment, the extracorporeal fixation device 16 slides over a plurality of bumps or detents on the cannula 10 exterior surface. These bumps or detents serve to prevent axial motion of the extracorporeal fixation device except under substantial selective manual force. The extracorporeal fixation device 16 may additionally have a ratcheting mechanism that allows for axial motion toward the patient but prevents motion in the reverse direction away from the patient.

The extracorporeal fixation device is useful to retain not only drainage tubes but also any type of catheter in place in the patient.

Once the catheter 10 is placed in the patient's chest, the bidirectional valve 14, which is normally closed, prevents pneumothorax from occurring. The normally closed, bidirectional valve 14 seals the drainage lumen 32. When the medical personnel require chest drainage, the bidirectional valve 14 is enabled or opened to allow fluid, air and contaminants to drain from the chest drainage tube 10.

In one embodiment, the valve-enabling lumen 34 is connected through the valve-enabling adapter 26 to a vacuum system. The typical vacuum system is operated by an electrical vacuum pump and regulator to maintain a low level vacuum of 1 to 100 mm Hg. Preferably, the vacuum is maintained at a level of 1 to 20 mm Hg.

When the vacuum system is activated, a vacuum is drawn through the valve-enabling lumen 34 and the bidirectional valve 14 opens. Stopping the vacuum system causes the bidirectional valve 14 to close and seal the drainage lumen 32.

The preferred vacuum activated, bidirectional valve embodiment 14 is one or more balloons mounted within the drainage lumen 32 of the cannula 10. More preferably, the balloons 14 are exposed to the drainage lumen 32 but reside within the optional valve housing 15 that is larger than the diameter of the drainage lumen 32. The collapsed balloons 14 reside within the housing 15 and do not impinge on the drainage lumen 32 where they could impede passage of the trocar 40 or 54. The balloons 14 are maintained in their collapsed state and out of the drainage lumen 32 by application of a vacuum through the valve-enabling adapter 26 and the valve-enabling lumen 34. An optional stopcock on the valve-enabling adapter 26 is closed to maintain the vacuum until it is desired to close the bidirectional drainage lumen seal 14. The valve housing 15 is fabricated, preferably, from transparent materials in order to allow for visualization of valve function and verification of drainage lumen patency. The balloons 14 are made with open cell foam. Such open cell foams are typically made from polyurethane materials and the spaces between the cells in the foam interconnect. The skin or surface of the balloon 14 is a fluid impermeable, elastomeric material such as latex, polyurethane, silastic, silicone elastomer and the like.

The balloons 14 are inflated, thus closing the bidirectional valve 14, by resilient expansion of the foam after fluid is allowed to flow back into the collapsed balloons. This may be done by removal of the vacuum or by opening the stopcock. When the bidirectional valve 14 is closed, drainage through the drainage lumen 32 stops and the chest opening is sealed. The bidirectional valve 14 is opened by application of a vacuum to the valve enabling lumen 34. The vacuum system can be operably connected to the same vacuum system used for drainage of the thorax. In this way, the bidirectional valve 14 automatically opens when drainage is activated.

Other bidirectional valve embodiments 14 include balloons that are normally deflated and open. These bidirectional valves 14 require that positive pressure be applied to inflate the balloons and occlude the drainage lumen 32. Removal of the pressure or application of a vacuum causes the balloons to deflate and the bidirectional valve 14 to open. Such bidirectional valves 14 do not require the use of open cell foam cores but may require external devices to monitor drainage lumen parameters and ensure patient safety.

In another embodiment, the bidirectional valve or seal 14 is made from a soft rubber or polymer. A central hole, slit or cross in the bidirectional valve 14 allows for generation of potential space in this normally closed structure. In this embodiment, insertion of a hollow obturator through the valve-enabling adapter 26 and the central hole, slit or cross opens the bidirectional valve 14, permitting fluid, air and contaminants to pass through the hollow obturator.

In yet another embodiment, the valve or seal 14 is a duckbill or one-way valve permitting fluid, air and contaminants to flow from the chest but not permitting introduction of air into the chest. When the trocar 40 or 54 is advanced into the cannula 10, the valve leaflets are moved into the open position to permit passage. This operation may be performed manually or automatically when trocar 40 or 54 insertion is required. The duckbill valve is typically fabricated from soft polymer materials such as silicone rubber, polyvinyl chloride, polyurethane and the like. The duckbill valve is preferably coated with materials such as heparin or silicone that prevent thrombosis and prevent unwanted permanent sealing of the valve leaflets.

Figure 5A:
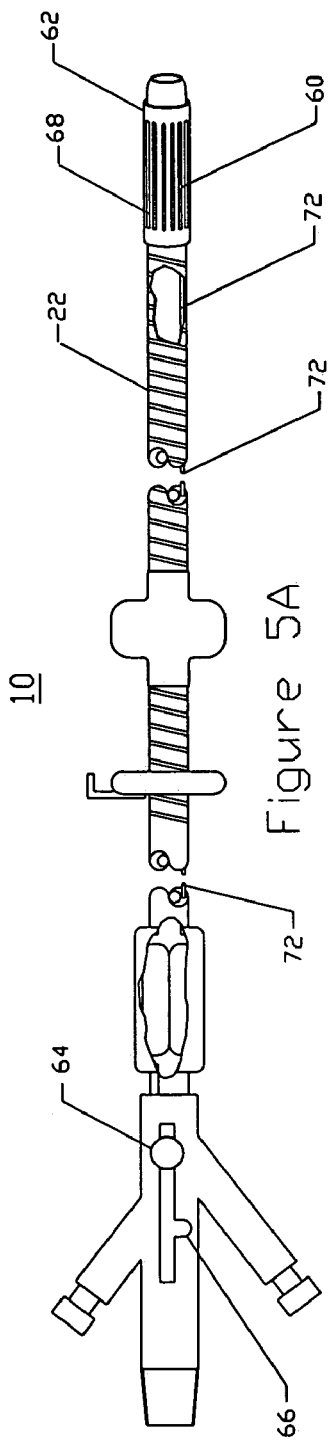
FIG. 5A illustrates the cannula with the selectively openable, slotted distal drainage apparatus, wherein the slots are closed, according to aspects of an embodiment of the invention.
Figure 5B:
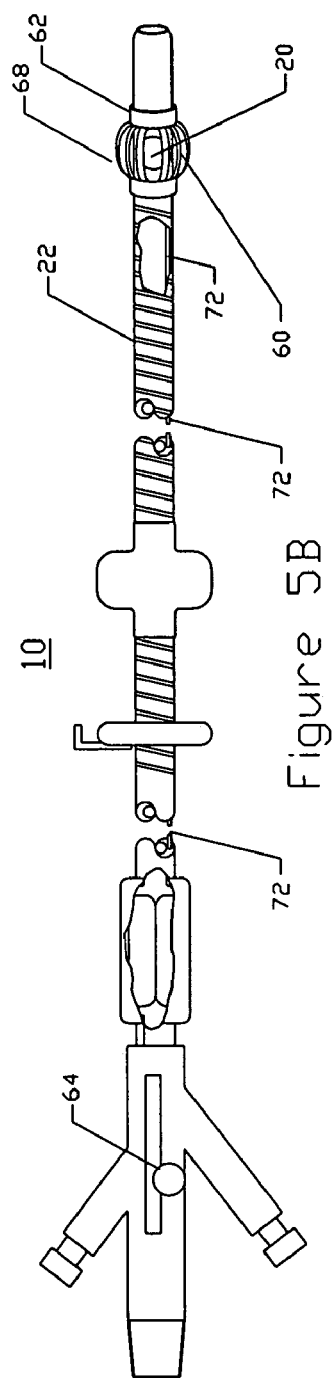
FIG. 5B illustrates the cannula with the selectively openable, slotted distal drainage apparatus, wherein the slots are opened, according to aspects of an embodiment of the invention.
Figure 5C:
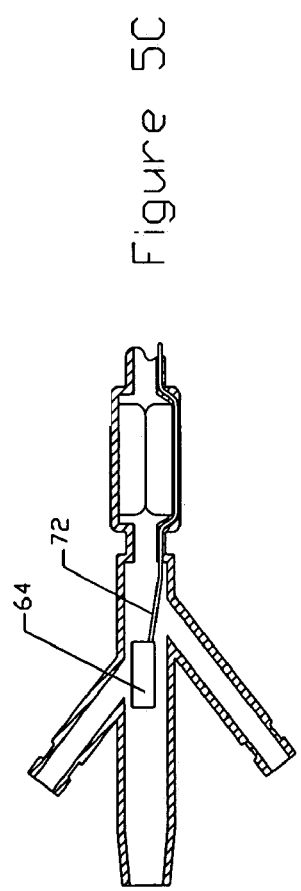
FIG. 5C illustrates a vertical cross section of the proximal end of the cannula, according to aspects of an embodiment of the invention.

FIG. 5A, FIG. 5B, and FIG. 5C illustrate another embodiment of the drainage holes 20 at the distal end of the catheter 10. FIG. 5A shows the catheter 10 comprising a knob, lever, or handle 64, a lock 66, a control rod 72, and a sleeve 68. The sleeve 68 comprises a series of longitudinal slits or slots 60 and a rigid ring 62. The proximal end of the sleeve 68 is affixed to the catheter 10 and the distal end of the sleeve terminates in the rigid ring 62 that slides over the catheter 10. The sleeve is located over the plurality of drainage holes 20 at the distal end of the catheter 10. The slits or slots 60 are disposed circumferentially around the sleeve 68. The sleeve 68 is located approximately 20 cm or less from the distal end of the tubing 22 and is preferably located 10 cm or less from the distal end of the tubing 22. The slots 60 are approximately 10 cm or less long and preferably 5 cm or less long. The slits or slots 60 are approximately 90 degrees apart and are preferably 45 degrees apart. The rigid ring 62 is operably attached to a control rod 72 running through one of the lumens of the multi-lumen tubing 22 and extending to the proximal end of the cannula 10. As shown in FIG. 5C, the control rod 72 is terminated at the proximal end of the cannula 10 with the knob, handle or lever 64 for manual activation. In FIG. 5A, the slots 60 are closed.

FIG. 5B shows the distal tip of the cannula 10 when the control rod 72 is retracted and the slots 60 are open. As the control rod 72 is retracted proximally, the distal ring 62 moves proximally, and the slits or slots 60 expand radially and increase their opening size, thus exposing the drainage holes 20 and providing drainage. The control rod 72 may serve an additional purpose of activating the intracorporeal fixation device 18. The lock 66 at the proximal end of the cannula 10 causes the control rod 72 to maintain its position until reversal is desired. The optional lever 64 provides mechanical advantage and makes it easier to move the control rod 72.

In another embodiment, the slots 60 are located in the wall 38 of the multi-lumen tubing 22 and connect the exterior of the catheter 10 with the drainage lumen 32, replacing the drainage holes 20. As the control rod 72 is retracted proximally, the slits or slots 60 expand radially and increase their opening size, thus providing drainage.

In a further embodiment, the cannula 10 of the present invention comprises at least one flexible control rod 72 extending from the distal tip of the cannula 10 to the proximal end of said cannula 10. The control rods 72 are slideably disposed within one of the lumens of the multi-lumen tubing 22. The control rods 72 are disposed off-center and terminate at or near the proximal end of the cannula 10 with a handle. The control rods 72 are fabricated from wire, polymer fiber or other flexible material. The cannula 10 further comprises an area of increased flexibility proximal to the distal attachment point of the control rod 72 to the cannula 10.

By withdrawing the control rod or rods 72 proximally, the cannula tip may be made to bend in a controlled direction in the area of increased flexibility. Such selective steerability is useful in advancing the cannula 10 through tortuous anatomy.

The cannula 10 of the present invention is useful during or after many thoracic surgeries and will benefit many patients in the emergency setting. The system is easier to place in the patient than standard chest drainage tubes and may be placed by personnel with less training than physicians (e.g. paramedics). The system is less likely to be misused than standard chest drainage tubes.

The cannula 10 of the present invention may be used for abdominal drainage, thoracic drainage, peritoneal dialysis and other procedures. The invention is not limited solely to thoracic procedures but to general mammalian body cavity drainage and/or catheterization.

The present invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method of draining of fluid, air and contaminants from a thoracic cavity of a mammalian patient comprising: inserting a tapered blunt tip of a flexible trocar and a distal end of an axially elongate tube into an incision into a thoracic cavity of a mammalian patient, wherein the flexible trocar is pre-inserted through a drainage lumen of a pre-attached, bidirectional, non-removable valve attached to a proximal end of the axially elongate tube and through a drainage lumen of the axially elongate tube and extends substantially the length of the axially elongate tube; selectively bending a region near the distal tip of the axially elongate tube while advancing the axially elongate tube into the thoracic cavity, wherein the bending steers the axially elongate tube into the thoracic cavity during insertion; removing the flexible trocar through the valve from the drainage lumen of the axially elongate tube and the drainage lumen of the valve; and selectively opening or closing the valve to control influx and efflux of fluid, air or contaminants into the thoracic cavity through the drainage lumen of the axially elongate tube.

2. The method of claim 1 wherein said bending of the axially elongate tube is controlled from the proximal end of said axially elongate tube whereby tortuous anatomy can be navigated.

3. The method of claim 1 wherein said bending of said axially elongate tube is caused by retraction of a control rod.

4. The method of claim 1 wherein said bending of said axially elongate tube is caused by electrical activation of a plurality of shape-memory actuators acting in opposition, wherein one actuator is enabled simultaneously with the opposing actuators not being activated.

5. The method of claim 1 wherein the step of selectively bending a region near the distal tip of the axially elongate tube is replaced by the steps of: inserting a hollow needle into the thoracic cavity; inserting a guidewire through the hollow needle into the thoracic cavity; removing the hollow needle following placement of the guidewire; advancing the chest drainage tube, comprising a flexible trocar, further comprising a tapered, blunt distal tip and a guidewire lumen extending the length of the trocar, into the thoracic cavity over the guidewire; and removing the trocar.

6. The method of claim 5 wherein said chest drainage tube is pre-mounted to said trocar.

7. The method of claim 5 wherein said chest drainage tube is subsequently fixed in position relative to the opening in the chest wall.

8. A method of draining of fluid, air and contaminants from a patient'thoracic cavity comprising: inserting a hollow needle into an incision into the thoracic cavity of a patient; inserting a guidewire through the hollow needle into the thoracic cavity; removing the hollow needle after inserting the guidewire; pre-attaching a non-removable, bidirectional valve, further comprising a drainage lumen and a valve control lumen, to the proximal end of an axially elongate tube, wherein the axially elongate tube comprises a proximal end, a distal end, and a drainage lumen extending substantially the axial length of the axially elongate tube; inserting a flexible trocar comprising a tapered, blunt distal tip, and a guidewire lumen extending the length of the flexible trocar, through a drainage lumen of the valve, into the proximal end of the axially elongate tube and into the drainage lumen of the axially elongate tube until the tapered distal tip extends beyond the distal end of the axially elongate tube; inserting a distal end of the axially elongate tube, comprising the pre-inserted, blunt flexible trocar and pre-attached bidirectional valve, over the guidewire and through the incision into the thoracic cavity of the patient, wherein the distal end of the axially elongate tube is advanced into the thoracic cavity of the patient; removing the flexible trocar from the drainage lumen of the axially elongate tube and from the drainage lumen of the valve; selectively opening or closing the drainage lumen of the valve, to control the influx and efflux of fluid, air or contaminants into the thoracic cavity through the drainage lumen of the axially elongate tube; and removing the guidewire after inserting the axially elongate tube.

9. The method of claim 8 further comprising selectively bending a region of increased flexibility near the distal tip of the axially elongate tube while advancing the tube into the chest cavity.

10. The method of claim 8 wherein the axially elongate tube further comprises a sideport, operably connected to the drainage lumen, wherein said sideport is located near the distal end of the axially elongate tube.

11. The method of claim 8 wherein the valve is pre-attached to the axially elongate tube near the proximal end of the axially elongate tube, prior to removal of the axially elongate tube from a package.

12. The method of claim 8 further comprising the step of advancing an extracorporeal fixation device distally along the axially elongate tube so that the extracorporeal fixation device is adjacent the thoracic wall of the patient and then locking the extracorporeal fixation device to prevent axial movement of the extracorporeal fixation device along the axially elongate tube.

13. The method of claim 8 further comprising the step of activating an intracorporeal fixation device, said intracorporeal fixation device being affixed to the axially elongate tube.

14. The method of claim 13, wherein the step of activating the intracorporeal fixation device comprises inflating a balloon through a balloon inflation port located substantially near the proximal end of the axially elongate tube.

15. The method of claim 8, wherein the step of selectively opening the valve comprises drawing a vacuum within the valve enabling lumen, said valve enabling lumen being operably separated and not connected to the drainage lumen of the valve, to open the valve.

16. The method of claim 15, wherein the step of selectively closing the valve comprises removing a vacuum from within a valve enabling lumen so that an open celled foam can expand to close the valve.

17. The method of claim 8 wherein the valve is a normally closed valve.

18. A method of draining of fluid, air and contaminants from a thoracic cavity of a mammalian patient comprising: inserting a chest drainage apparatus into a thoracic cavity of a mammalian patient, wherein the chest drainage apparatus comprises an axially elongate tube with a pre-inserted flexible trocar having a tapered, blunt distal tip, further wherein the flexible trocar is pre-inserted through a pre-attached, non-removable, bidirectional valve, attached to a proximal end of the axially elongate tube, and through a drainage lumen of the axially elongate tube and extends substantially the length of the axially elongate tube; advancing the chest drainage apparatus to its target location within the thoracic cavity; removing the flexible trocar from the drainage lumen of the valve and the axially elongate tube; and selectively opening or closing the valve to control influx and efflux of fluid, air or contaminants into the thoracic cavity through the drainage lumen of the axially elongate tube.

19. The method of claim 8 further comprising the step of activating an internal fixation device, said internal fixation device being pre-attached to the axially elongate tube, following placement of the distal end of the axially elongate tube within the thoracic cavity.

20. The method of claim 8 further comprising the step of activating an internal fixation device, said internal fixation device comprising a balloon which is pre-attached to the axially elongate tube, the activation step being accomplished by application of fluid pressure at the proximal end of the axially elongate tube, said fluid pressure causing inflation of the balloon.

* * * * *